United States Patent
Mahdjoubi Namin et al.

(10) Patent No.: US 10,053,841 B2
(45) Date of Patent: Aug. 21, 2018

(54) APPARATUS AND HANDHELD SHOWER UNIT THEREOF FOR WATER SUPPLY AND SANITARY PURPOSES, E.G. FOR ALLOWING PURIFICATION AND EITHER RECYCLING OF WATER OR DISCARDING OF WATER

(71) Applicant: ORBITAL SYSTEMS AB, Malmö (SE)

(72) Inventors: Amir Mehrdad Mahdjoubi Namin, Malmö (SE); Esbjörn Beckmann, Malmö (SE)

(73) Assignee: ORBITAL SYSTEMS AB, Malmo (SE)

(*) Notice: Subject to any disclaimer, the term of this patent is extended or adjusted under 35 U.S.C. 154(b) by 0 days.

(21) Appl. No.: 15/519,487

(22) PCT Filed: Nov. 12, 2015

(86) PCT No.: PCT/SE2015/051199
§ 371 (c)(1),
(2) Date: Apr. 14, 2017

(87) PCT Pub. No.: WO2016/076784
PCT Pub. Date: May 19, 2016

(65) Prior Publication Data
US 2017/0226720 A1 Aug. 10, 2017

(30) Foreign Application Priority Data

Nov. 14, 2014 (SE) ........................................ 1451368
Jun. 5, 2015 (SE) ........................................ 1550738

(51) Int. Cl.
A47K 3/00 (2006.01)
E03C 1/04 (2006.01)
(Continued)

(52) U.S. Cl.
CPC ............ *E03C 1/0409* (2013.01); *A47K 3/281* (2013.01); *E03C 1/126* (2013.01); *G01N 33/18* (2013.01)

(58) Field of Classification Search
CPC ........................................................ E03C 1/06
(Continued)

(56) References Cited

U.S. PATENT DOCUMENTS

2006/0005311 A1 1/2006 Fentrouci
2009/0261282 A1 10/2009 Connors

FOREIGN PATENT DOCUMENTS

DE 202005020753 U1 7/2006
FR 2792701 A1 10/2000
(Continued)

OTHER PUBLICATIONS

International Search Report dated Feb. 24, 2016 for PCT Application No. PCT/SE2015/051199.

*Primary Examiner* — Lori Baker
(74) *Attorney, Agent, or Firm* — Moser Taboada

(57) ABSTRACT

The present invention describes an apparatus (1) for water supply and sanitary purposes, e.g. for allowing purification and either recycling of water or discarding of water, wherein the apparatus (1) comprises an on/off unit (2) comprising a battery (3) and a transceiver (4), and wherein the on/off unit (2) is activable by pushing an on/off knob (5) of the on/off unit (2) rendering the transceiver (4) to transmit a wireless signal to a control system to turn the apparatus (1) on respective off. Furthermore, the present invention also relates to an apparatus (1) for water supply and sanitary purposes, wherein the apparatus (1) is a shower device (1) comprising a handheld shower unit (9) having a magnetic valve (8), and also comprising a holder unit (10) for holding the handheld shower unit (9) when not being used, wherein a magnet (11) is arranged in the holder unit (10) or the (Continued)

handheld shower unit (9), and wherein an activation sensor (12) is provided in the holder unit (10) or in the handheld shower unit (9) so that the magnetic valve (8) is turned into an open position when the handheld shower unit (9) is removed from the holder unit (10), and wherein the holder unit (10) holds the magnetic valve (8) in a closed position when the handheld shower unit (9) is held by the holder unit (10) and not being used. Moreover, the present invention is also related to a handheld shower unit (9) for an apparatus (1).

19 Claims, 3 Drawing Sheets

(51) Int. Cl.
   *A47K 3/28* (2006.01)
   *E03C 1/126* (2006.01)
   *G01N 33/18* (2006.01)
(58) Field of Classification Search
   USPC .................................................. 4/615–618
   See application file for complete search history.

(56) References Cited

FOREIGN PATENT DOCUMENTS

| WO | WO-2004101902 A1 | 11/2004 |
| WO | WO-2007059051 A2 | 5/2007 |
| WO | WO-2013095278 A1 | 6/2013 |

APPARATUS AND HANDHELD SHOWER UNIT THEREOF FOR WATER SUPPLY AND SANITARY PURPOSES, E.G. FOR ALLOWING PURIFICATION AND EITHER RECYCLING OF WATER OR DISCARDING OF WATER

FIELD OF THE INVENTION

The present invention relates to an apparatus for water supply and sanitary purposes, such as e.g. for allowing purification and either recycling of water or discarding of water.

TECHNICAL BACKGROUND

Devices for water supply and sanitary purposes which involves purification and recycling or discarding of water are known. One such example, called a hybrid device, is disclosed in WO 2013/095278. In WO 2013/095278 there is disclosed a hybrid device for a recirculation shower, allowing purification and either recycling of water or discarding of water, said hybrid device comprising a recirculation loop, a filter system with a nano-filter, at least one filter quality sensor, and at least one pre-filter, said hybrid device being arranged to redirect the water from recirculation to drainage when the at least one filter quality sensor indicates the need thereof.

One aim of the present invention is to provide an improved apparatus for water supply and sanitary purposes, which apparatus is easier to control and install for the user.

SUMMARY OF ONE ASPECT OF THE INVENTION

The stated purpose above is achieved by an apparatus for water supply and sanitary purposes, wherein the apparatus comprises an on/off unit comprising a battery and a transceiver, and wherein the on/off unit is activable by pushing an on/off knob of the on/off unit rendering the transceiver to transmit a wireless signal to a control system to turn the apparatus on respective off.

According to specific embodiment, the present invention allows purification and either recycling of water or discarding of water. With respect to a full expression of "an apparatus for water supply and sanitary purposes allowing purification and either recycling of water or discarding of water" it should be noted that examples of such an apparatus are inter alia a shower, toilette or sink, but may also be any other such form. As mentioned above, the expression "hybrid device" is another alternative which has been used with linkage to the ability of "allowing purification and either recycling of water or discarding of water".

The power source incorporated in the apparatus according to the present invention may be of different type. According to one specific embodiment, the on/off unit comprises a microturbine. In this case, the microturbine is a power source being arranged to generate power when a water flow passages the microturbine. In the case of incorporating a microturbine, then the battery involved may e.g. be a rechargeable battery which is recharged by the power generated.

The present invention has several advantages. First of all, it is very easy for a user to start and stop the apparatus, such as e.g. a shower, when only an on/off knob is needed and wireless communication is used. Secondly, the present invention also brings about a less need of cabling and also opens up for use of different types of power sources. Moreover, as there is a control system which is in connection with the apparatus, user data may be logged. Such used data may e.g. in the case of a shower hybrid device comprise water usage over time and per shower occurrence, and time used and amount of water used during water recirculation and water discarding, respectively, per shower and over time. Another parameter may e.g. be water temperature, and there are of course several other possible examples.

In this context it may be mentioned that there are existing display devices. For instance in US 2009/0106891 there is disclosed a display apparatus for affixation to a shower or bath water supply piping or incorporated within a shower. The display apparatus includes a power generation, CPU or microprocessor, temperature sensor and/or water flow sensors, timing circuits and a display means. The assembly according to US 2009/0106891 may have a shut off mechanism and the water shut off means is electrically connected to the CPU or microprocessor and the power means such that the computer controls the application of electrical power to activate or de-activate the water shut off means.

According to the present invention there is incorporated a transceiver which is arranged to transmit a wireless signal to a control system to turn the apparatus on and off when the on/off knob is activated and deactivated, respectively. This is not the case with the device disclosed in US 2009/0106891. Although the display means according to one embodiment of US 2009/0106891 is said to be located remotely from the sensor and CPU or microprocessor with data transfer means communicated wirelessly, there is not disclosed a system comprising a transceiver which transmits a wireless signal to a control system so that the apparatus is turned on and off when an on/off unit is activated by pushing an on/off knob, such as according to the present invention.

The present invention also provides several other advantages, such as for instance in relation to the installation operation of a final product. By minimizing the cabling there is less work to be done by the plumber, electrician or home user, and this renders a more reliable end product and user experience. This is of great importance as all apparatus for water supply and sanitary purposes are installed by professionals, or sometimes amateurs, and their work influences the end result and the user experience directly.

Today solutions which are built into walls are very difficult to provide with devices for water supply and sanitary purposes in need of electricity, such as for powering a pump used in the system. This is a result of the fact that providers, e.g. heating, ventilation and sanitation system providers, are not comfortable in cabling electric cable in walls. This entire problem is solved by the present invention.

SPECIFIC EMBODIMENTS AND OTHER ASPECTS OF THE INVENTION

Figure 1:
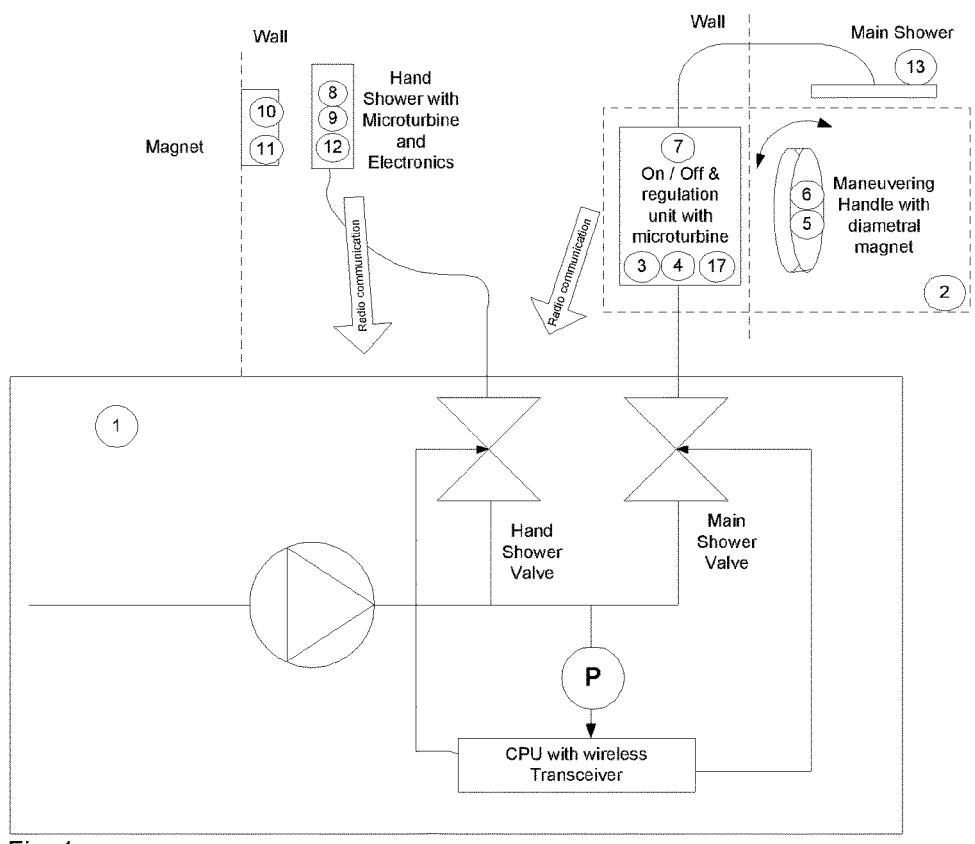
In FIG. 1 there is shown a block diagram of one specific embodiment of a shower apparatus according to the present invention.

Below, there are discussed other aspects and different specific embodiments of the present invention.

Many sanitary devices may also include a handheld unit. For instance many showers include both a top (or rain) shower and also a handheld shower unit.

Yet another aim of the present invention is to provide an improved apparatus for water supply and sanitary purposes, which apparatus includes a handheld shower unit. More specific, the present invention according to this aspect is directed to an apparatus for water supply and sanitary purposes having both a top shower unit and a handheld shower unit where the handheld shower unit is optimized for such an apparatus.

The stated purpose above is achieved by an apparatus for water supply and sanitary purposes, e.g. which allows purification and either recycling of water or discarding of water, wherein the apparatus comprises a handheld shower unit and a holder unit for holding the handheld shower unit when not being used, wherein the holder unit comprises a battery and a transceiver, and wherein the transceiver transmits a wireless signal when the handheld shower unit is removed from the holder unit rendering a water supply valve for the handheld shower unit to open, and wherein the transceiver transmits a wireless signal when the handheld shower unit is placed into the holder unit again rendering the water supply valve for the handheld shower unit to close.

There are several advantages related to the present invention according to this aspect. First of all, the apparatus provides a simple and secure way of controlling a handheld shower unit which is operated electronically. Secondly, the present invention provides an arrangement which is easy to install and maintain for a sanitation technician. For instance, the water supply valve for the handheld shower unit may be arranged in a shower box arranged beneath the shower floor, and hence not in the wall behind a shower according to the present invention. Fact is that the present invention provides a solution where no such parts or electrical parts have to be arranged in the wall behind the shower.

Moreover, with respect to the expression "an apparatus for water supply and sanitary purposes allowing purification and either recycling of water or discarding of water" it should be noted that examples of such an apparatus are inter alia a shower, toilette or sink, but may also be any other such form. As mentioned above, the expression "hybrid device" is another alternative which has been used with linkage to the ability of "allowing purification and either recycling of water or discarding of water".

Furthermore, it should be noted that automatic switch function between a handheld shower unit and a top shower has been described before. For instance in CN202460903U there is disclosed one type of automatic switchover water shower. The present invention, however, is directed to providing a handheld shower unit which via operation, namely by detaching or returning the handheld shower unit from and into the holder unit, controls a valve for opening and closing, respectively, by use of wireless communication. This is very different from an automatic switch function as such.

According to one specific embodiment of the present invention, a control system is arranged to activate the water supply valve for opening and closing, respectively, when the transceiver transmits a wireless signal to said control system. The use of a control system in the apparatus according to the present invention is further discussed below.

The present invention finds special use in a shower apparatus having at least one more nozzle in addition to the handheld shower unit. One typical example is a shower having a top shower unit and a handheld shower unit. By removing the handheld shower unit from the holder unit the user has activated this path and when the on/off knob or the like then is turned on, then the water flow is directed to the handheld shower. Furthermore, if the handheld shower unit then is placed into the handheld shower unit again and the valve is closed, then all of the water flows from the top shower is the shower is set in "on mode".

Figure 2:
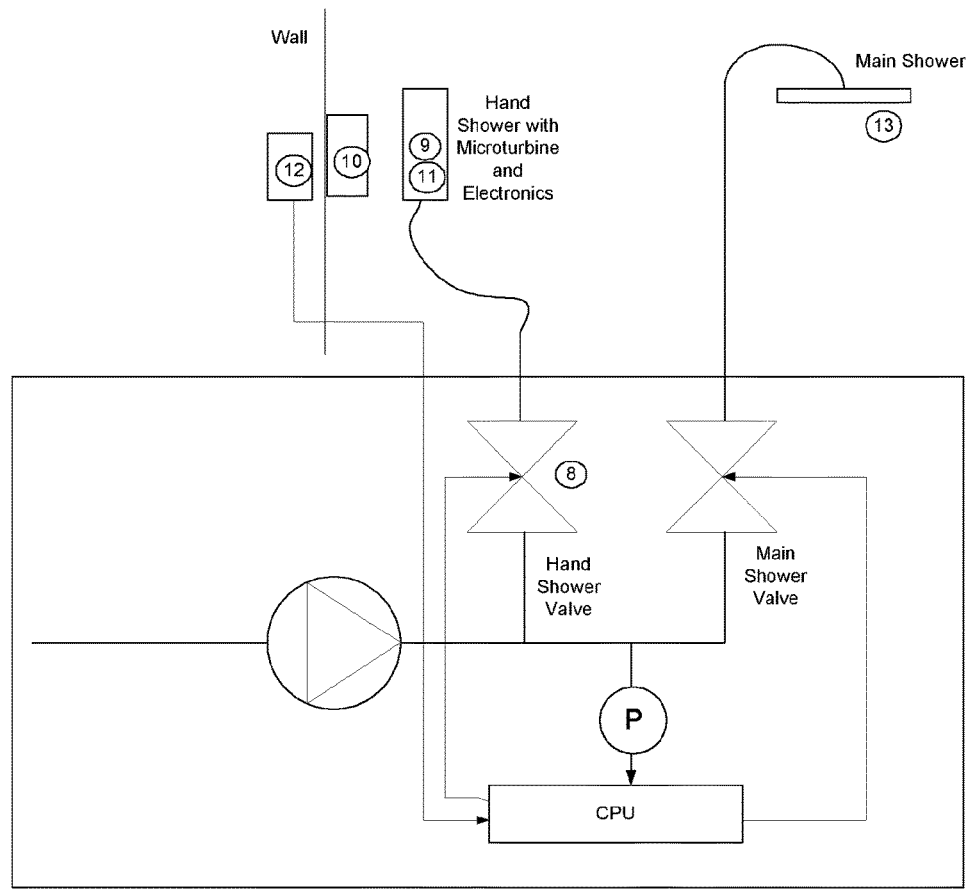
In FIG. 2 there is shown a block diagram of another embodiment of a shower apparatus according to the present invention.

The actual switch function of the handheld shower unit and holder unit may be of different type. According to one specific embodiment, there is one magnet provided in the handheld shower unit and one switch unit in the holder unit which together provides a magnetic on/off switch. According to this embodiment these two units function as the actual switch promoting the opening and closing of the water supply valve for the handheld shower unit. Furthermore, according to another specific embodiment, there is one holder magnet provided in the handheld shower unit and one holder magnet in the holder unit, said holder magnets attracting one another for secure attachment. These two units function as the attracting units holding them together when being in contact. It may further be noted that according to a combination of the embodiments disclosed above, which is also shown in FIG. 2, there are two magnets provided in the handheld shower unit. These two magnets are arranged separately. It may also be possible to provide them together as one single magnet, but then it is important to arrange for a smart magnet where two different portions can have different functions, one portion for holding and one portion for the switch function. With two different magnets in the handheld shower this functionality is provided by arrange two magnets with different magnetic poles. As such, they can act totally separately.

As mentioned above, the apparatus according to the present invention may have an on/off knob being part of an on/off unit and may also comprise a control system providing operational control. According to one specific embodiment of the present invention, the apparatus also comprises an on/off knob constituting an on/off unit comprising a second battery and second transceiver, and wherein the on/off unit is activable by pushing the on/off knob of the on/off unit rendering the second transceiver to transmit a wireless signal to the control system to turn the apparatus on respective off. As may be understood, the actual on/off knob is the actual unit activating water to flow out from the apparatus (on mode) or deactivating the apparatus (off mode). When the handheld shower is removed from the holder unit and the on/off knob is turned on, then water flows out from the handheld shower unit.

The on/off knob according to the present invention may be in the type of a smart on/off knob. When the apparatus is deactivated and the on/off knob is set into "resting position", then the battery may be tuned off automatically. As such, a battery in the on/off knob can last for a very long time.

In relation to this it may be noted that the power source incorporated in the apparatus according to the present invention may be of different type. According to one specific embodiment of the present invention, the transceiver(s) is low-power transceiver(s). As one example, Bluetooth technology may be implemented in the apparatus according to the present invention.

The apparatus disclosed above according to the present invention has several advantages. First of all, it is very easy for a user to start and stop the apparatus, such as e.g. a shower, when only an on/off knob is needed and wireless communication is used. Secondly, the present invention also brings about a less need of cabling and also opens up for use of different types of power sources. Moreover, as there is a control system which is in connection with the apparatus, user data may be logged. Such used data may e.g. in the case of a shower hybrid device comprise water usage over time and per shower occurrence, and time used and amount of water used during water recirculation and water discarding, respectively, per shower and over time. Another parameter may e.g. be water temperature, and there are of course several other possible examples.

The apparatus disclosed above according to the present invention also provides several other advantages, such as for instance in relation to the installation operation of a final product. By minimizing the cabling there is less work to be done by the plumber, electrician or home user, and this renders a more reliable end product and user experience. This is of great importance as all apparatus for water supply and sanitary purposes are installed by professionals, or sometimes amateurs, and their work influences the end result and the user experience directly. Today solutions which are built into walls are very difficult to provide with devices for water supply and sanitary purposes in need of electricity, such as for powering a pump used in the system. This is a result of the fact that providers, e.g. heating, ventilation and sanitation system providers, are not comfortable in cabling electric cable in walls. This entire problem is solved by the present invention.

According to another specific embodiment of the present invention, the on/off unit comprises a magnet and an electric sensor responding to magnetic angle, where a provided magnetic field is controllable by rotating a rotatable on/off knob, and where the rotating of the on/off knob changes a temperature value being sent from the wireless transmitter to the control system. According to this embodiment, the magnitude of the magnetic field responds to a set point of the temperature.

Furthermore, according to yet another specific embodiment, the on/off unit comprises an accelerometer and/or gyrometer. The accelerometer or gyrometer provides for the functionality of having an on/off knob that knows its position, i.e. is calibrated with reference to its position. As such, if the knob is rotated when being placed or being permanently fixated on the wall the knob may react to this rotation based on the change in its position.

As understood from above, the present invention also provides the advantage that the electronics may be arranged suitably depending on the specific device and application of the present invention. Exactly how to arrange the circuit(s) in a device according to the present invention may vary and depends on the intended application. As an example, the electronic parts may be arranged in the wall or e.g. in the handheld shower unit which is explained below.

According to one specific embodiment of the present invention, the on/off unit comprises a mechanical on/off switch comprising a spring responding to activation by pushing the on/off knob of the on/off unit. According to another embodiment, the on/off unit comprises an on/off switch responding to strength of magnetic field. In this case there is no need for a mechanical on/off switch, but instead only a minor touch on the on/off knob provides the creation of a magnetic field. By having a switch responding to change of strength of magnetic field the activation and also deactivation may be performed by touching, such as e.g. via pushing, the on/off knob.

In relation to the present invention it is important to understand that the on/off knob can be in any possible and suitable shape. According to one specific embodiment of the present invention, the on/off unit comprises a docking unit and/or one or more suction cup(s). In the case of a docking unit, then the on/off knob has an intended place to be linked to, at least when being used. The on/off knob may, however, have e.g. suction cup(s) so that it may be attached to a wall, such as a shower wall, in more or less any place, and at that position also then be activated or deactivated by a user. Other possibilities for attachment of the on/off knob are tape, screws or glue or other regular attachment means.

According to another aspect of the present invention there is disclosed an apparatus for water supply and sanitary purposes, wherein the apparatus is a shower device comprising a handheld shower unit having a magnetic valve, and also comprising a holder unit for holding the handheld shower unit when not being used, where a magnet is arranged in the holder unit or the handheld shower unit, and where an activation sensor is provided in the holder unit or in the handheld shower unit so that the magnetic valve is turned into an open position when the handheld shower unit is removed from the holder unit, and where the holder unit holds the magnetic valve in a closed position when the handheld shower unit is held by the holder unit and not being used. Also in this case, according to one embodiment the apparatus allows purification and either recycling of water or discarding of water.

This specific embodiment of the present invention may also be linked to the first aspect of the present invention disclosed above, such as an add-on together with an embodiment where there is an on/off knob of an on/off unit arranged which renders a transceiver to transmit a wireless signal to a control system to turn the apparatus on respective off when being pushed (activated or deactivated). Such a specific embodiment of the present invention is shown in FIG. 1

As notable from above, the magnet may be arranged in the holder unit or in the handheld shower unit. Both versions are possible according to the present invention. Moreover, the activation sensor may be provided in the holder unit or in the handheld shower unit, and the magnetic valve may be arranged in the handheld shower unit or in the water pipeline of the shower apparatus system. These alternatives are further explained with reference to the explanation below of the drawings.

In addition to the functionality of being turned on when the handheld shower unit is removed from the holder unit and turned off when being replaced to the holder unit, the apparatus may also have other functional properties. According to one specific embodiment of the present invention, the apparatus comprises a top shower unit having an overpressure relief valve. This additional feature with an overpressure relief valve may ensure that water only flows through the handheld shower when this is removed from the holder unit even if the shower apparatus also comprises the top shower unit. The overpressure relief valve may be mechanically or electronically controlled by pressure and/or flow.

It may further be mentioned that the apparatus according to the present invention also may have several other components which e.g. may be of interest in e.g. a hybrid shower device. Therefore, according to one embodiment of the present invention, the apparatus comprises a recirculation loop, a filter system and at least one water quality sensor. These components may be of interest to ensure an effective purification of the water used in a hybrid shower and may ensure a possibility for a system to measure the water quality and as such drive recirculation or discarding of the water. It may further be said that such a hybrid device according to the present invention may comprise several sensors, also of different type, such as e.g. conductivity sensors.

It should further be said that all possible combinations of the different aspects disclosed above are possible according to the present invention.

DETAILED DESCRIPTION OF THE DRAWINGS

In FIG. 1 there is shown a block diagram of one specific embodiment of a shower apparatus 1 according to the present invention. The apparatus 1 comprises an on/off unit 2 comprising a battery 3 and a transceiver 4. In this case, the on/off unit 2 also comprises a microturbine 17, but it should be noted that only a battery 3 may be provided as the single power source. The on/off unit 2 also comprises an on/off knob 5 comprising a magnet 6. An electric sensor 7 is further arranged in the on/off unit 2. By pushing the on/off knob 5, the on/off unit 2 is activated/deactivated so that the apparatus 1 is turned on and off, respectively.

Furthermore, according to the specific embodiment shown in FIG. 1 the apparatus 1 also comprises a handheld shower unit 9 having a magnetic valve 8. A holder unit 10 having a magnet 11 is arranged for holding the handheld shower unit 9 in place when not being used. An activation sensor 12 is in this case provided in the handheld shower unit 9. The magnetic valve 8 is turned into an open position when the handheld shower unit 9 is removed from the holder unit 10, and consequently held in a closed position when the handheld shower unit 9 is fixated to the holder unit 10. As one alternative example, the activation sensor 12 may be provided in the holder unit 10 instead of the handheld shower unit 9. Furthermore, in this case the apparatus 1 also comprises a main shower (a top shower unit) 13.

In FIG. 2 there is shown a block diagram of another specific embodiment of a shower apparatus 1 according to the present invention. In this case the magnetic valve 8 is not provided within the handheld shower unit 9, but instead within the water pipeline system. This arrangement provides an active concept for regulation the shower apparatus 1 when using the handheld shower unit 9.

Figure 3:
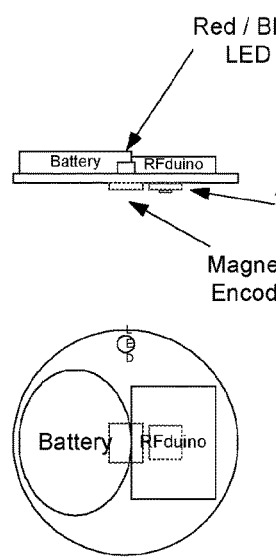
In FIG. 3 there is shown one part of an on/off unit according to one specific embodiment of the present invention.

In FIG. 3 there is shown one part of an on/off unit 2 according to one embodiment of the present invention. In this case, the on/off unit 2 comprises an on/off knob 5 having an activation button and a magnet 6. There is further arranged and a magnetic encoder, a battery 3, RFduino and LED component(s). With reference to FIG. 3 it may be noted that the actual on/off knob 5 may comprise several different parts which may be assembled to be used. This also opens up for the advantage of having different functionality in different parts of the on/off knob 5, such as the actual electrical parts in one part and the magnet in another part, or in the wall, etc. This implies that it is easier to reassemble the on/off knob 5 when any part must be replaced or the like. This is also an advantage of the present invention when being compared to known apparatus for water supply and sanitary purposes where replacement of parts requires much work and must often be done by professionals.

Figures 4A, 4B, 4C:
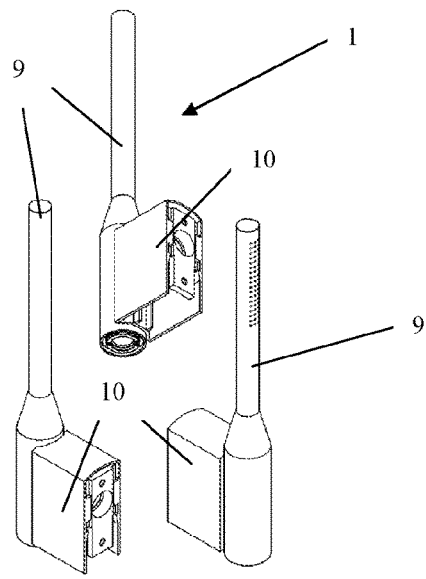
In FIG. 4a-c there are shown an apparatus according to one specific embodiment of the present invention, where the handheld shower unit and the holder unit is shown.

In FIG. 4a-c there are shown an apparatus 1 according to one specific embodiment of the present invention, where the handheld shower unit 9 and the holder unit 10 is shown. The handheld shower unit 9 is put together with the holder unit 10, and different types of views are shown.

Figure 5:
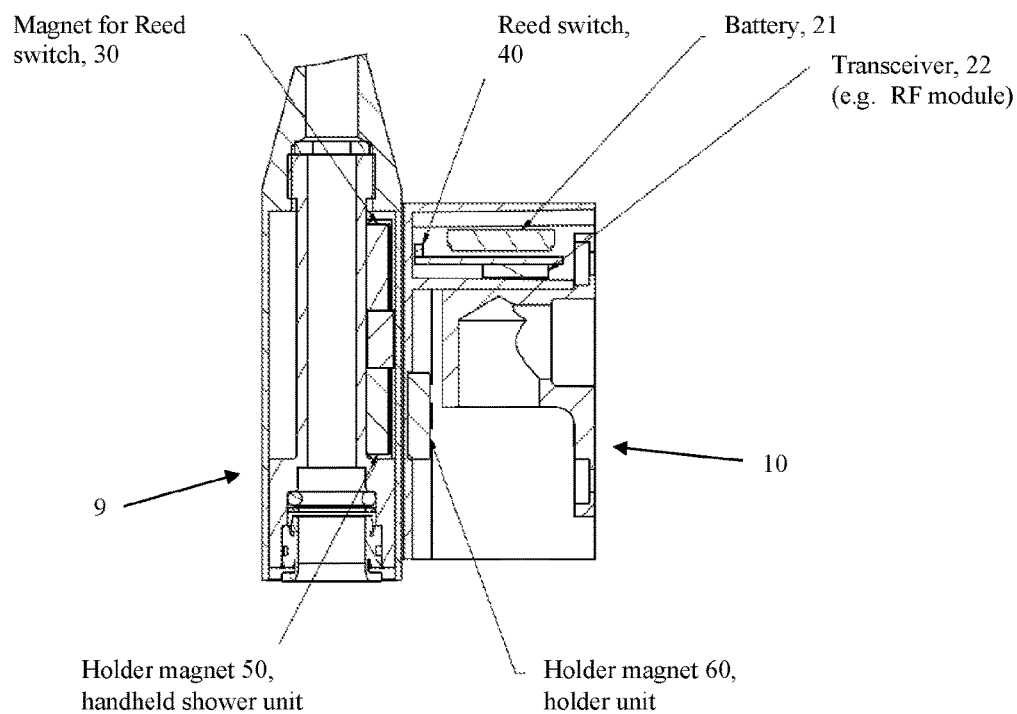
In FIG. 5 there is shown one specific embodiment of an apparatus according to the present invention, where part of the handheld shower unit and the holder unit are shown in a cross section.

In FIG. 5 there is shown a cross sectional view of one specific embodiment of a handheld shower unit 9 and a holder unit 10 put together. In the handheld shower unit 9 there is arranged two magnets, one switch magnet 30 and one holder magnet 50. In the holder unit 10 there is arranged one switch unit 40, here called "Reed switch", and one holder magnet 60. As may be understood, the two holder magnets 50, 60 act to hold the handheld shower unit 9 and the holder unit 10 together. The switch magnet 39 and the switch 40 are activating the transceiver 22 to send a signal so that the water supply valve is opened or closed. In FIG. 2 there is also shown a battery 21 in the holder unit 10.

The invention claimed is:

1. An apparatus for water supply and sanitary purposes, the apparatus comprising:
   a recirculation loop;
   a filter system;
   at least one water quality sensor;
   a control system; and
   an on/off unit comprising
      a battery,
      an off/off knob, and
      a transceiver;
   wherein the on/off unit is activable by pushing the on/off knob of the on/off unit rendering the transceiver to transmit a wireless signal to the control system to turn the apparatus on respective on or off state,
   wherein the apparatus conducts purification and either recycling of water or discarding of water.

2. An apparatus for water supply and sanitary purposes, the apparatus comprising:
   a recirculation loop;
   a filter system;
   at least one water quality sensor;
   a handheld shower unit; and
   a holder unit for holding the handheld shower unit when not being used, the holder unit comprising a battery and a transceiver,
   wherein the transceiver transmits a wireless signal when the handheld shower unit is removed from the holder unit rendering a water supply valve for the handheld shower unit to open,
   wherein the transceiver transmits a wireless signal when the handheld shower unit is placed into the holder unit again rendering the water supply valve for the handheld shower unit to close, and
   wherein the apparatus conducts purification and either recycling of water or discarding of water.

3. An apparatus according to claim 2 further comprising a control system arranged to activate the water supply valve for opening and closing, respectively, when the transceiver transmits a wireless signal to said control system.

4. An apparatus according to claim 2 further comprising at least one more nozzle in addition to the handheld shower unit.

5. An apparatus according to claim 2, wherein there is one magnet provided in the handheld shower unit and one switch unit in the holder unit which together provides a magnetic on/off switch.

6. An apparatus according to claim 2, wherein there is one holder magnet provided in the handheld shower unit and one holder magnet in the holder unit, said holder magnets attracting one another for secure attachment.

7. An apparatus according to claim 1 further comprising an on/off knob constituting an on/off unit, the on/off unit comprising a second battery and second transceiver, wherein the on/off unit is activable by pushing the on/off knob of the on/off unit rendering the second transceiver to transmit a wireless signal to the control system to turn the apparatus on respective on or off state.

8. The apparatus according to claim 7, wherein the on/off unit comprises a magnet and an electric sensor responding to magnetic angle, wherein a provided magnetic field is controllable by rotating a rotatable on/off knob, and wherein the rotating of the on/off knob changes a temperature value being sent from the wireless transmitter to the control system.

9. The apparatus according to claim 1, wherein the on/off unit also comprises a microturbine.

10. The apparatus according to claim 1, wherein the transceiver is a low-power transceiver.

11. The apparatus according to claim 1, wherein the on/off unit comprises a magnet and an electric sensor responding to magnetic angle, wherein a provided magnetic field is controllable by rotating a rotatable on/off knob, and wherein the rotating of the on/off knob changes a temperature value being sent from the wireless transmitter to the control system.

12. The apparatus according to claim 1, wherein the on/off unit comprises a mechanical on/off switch comprising a spring responding to activation by pushing the on/off knob of the on/off unit.

13. The apparatus according to claim 1, wherein the on/off unit comprises an on/off switch responding to strength of magnetic field.

14. The apparatus according to claim 1, wherein the on/off unit comprises an accelerometer and/or gyrometer.

15. The apparatus according to claim 1, wherein the on/off unit comprises a docking unit and/or one or more suction cup(s).

16. An apparatus for water supply and sanitary purposes, wherein the apparatus is a showering device, the apparatus comprising:

a recirculation loop;
a filter system;
at least one water quality sensor;
a handheld shower unit having a magnetic valve;
a holder unit for holding the handheld shower unit when not being used;
a magnets arranged in the holder unit or the handheld shower unit;
an activation sensor provided in the holder unit or in the handheld shower unit,
wherein the magnetic valve is turned into an open position when the handheld shower unit is removed from the holder unit,
wherein the holder unit holds the magnetic valve in a closed position when the handheld shower unit is held by the holder unit and not being used, and
wherein the apparatus conducts purification and either recycling of water or discarding of water.

17. The apparatus according to claim 1, wherein the apparatus is a showering device, the apparatus further comprising:

a handheld shower unit having a magnetic valve;
a holder unit for holding the handheld shower unit when not being used; wherein
a magnets arranged in the holder unit or the handheld shower unit;
an activation sensor provided in the holder unit or in the handheld shower unit,
wherein the magnetic valve is turned into an open position when the handheld shower unit is removed from the holder unit, and
wherein the holder unit holds the magnetic valve in a closed position when the handheld shower unit is held by the holder unit and not being used.

18. The apparatus according to claim 15 further comprising a top shower unit having an overpressure relief valve.

19. The apparatus according to claim 18, wherein the overpressure relief valve is mechanically or electronically controlled by pressure and/or flow.

* * * * *